United States Patent [19]

Lee et al.

[11] Patent Number: 4,478,945

[45] Date of Patent: Oct. 23, 1984

[54] METHOD FOR EVALUATING THYROID FUNCTION

[76] Inventors: Wai-Nang P. Lee, 6502 Ranchito Ave., Van Nuys, Calif. 91401; Michael D. Harpen, 3701 Caryhe Close, Apt. 989, Mobile, Ala. 36609; Jeffry A. Siegel, Dept. of Radiology, Medical Physical Division, Center, Los Angeles, Calif. 90024

[21] Appl. No.: 287,701

[22] Filed: Jul. 28, 1981

[51] Int. Cl.$^3$ ................... G01N 33/54; G01N 33/60; G01T 1/00
[52] U.S. Cl. .................................. 436/500; 436/541; 436/804; 436/824
[58] Field of Search ............... 436/500, 541, 804, 824; 424/1

[56] References Cited

U.S. PATENT DOCUMENTS 4,271,141 6/1981 Goedgmans .................. 436/500

OTHER PUBLICATIONS

Irvine, J. Clin. Endocrinol. Metab., 38:655-662 (1974).
Sutherland et al., J. Endocrinol., 65:319-332 (1975).
Harpen et al., J. Nucl. Med., 22:246-252 (1981).

Primary Examiner—Christine M. Nucker

[57] ABSTRACT

Clinical method for evaulating thyrometabolic function by determination of clinically important thyroxine concentrations and thyroxine binding protein capacities in plasma.

The method employs a competitive binding technique for determining free thyroxine concentration and thyroxine binding capacity for plasma having a known total thyroxine concentration.

10 Claims, 3 Drawing Figures

METHOD FOR EVALUATING THYROID FUNCTION

The invention described herein was made in the course of work under a grant or award from the Department of Health and Human Services.

The present invention relates generally to methods for evaluating thyroid function. More particularly, the present invention relates to an improved competitive binding procedure for determining biologically effective concentrations of clinically important thyroid hormones, the capacities of the hormone carriers, and thyroid binding proteins in plasma.

The fully developed human thyroid gland in found wrapped tightly around the anterior and lateral surfaces of the trachea and larnyx and includes two lobes giving it the appearance from the front of a butterfly. The thyroid gland manufactures the two thyroid hormones L-thyroxine (3,5,3',5'-L-tetraiodo-thyronine) and L-triiodothyronine (3,5,3'-L-triiodothyronine). These two hormones are commonly known as $T_4$ and $T_3$ respectively.

As the thyroid hormones diffuse into the blood, they are bound loosely to three proteins: an inter-alpha globulin (thyroxine-binding globulin, TBG) a prealbumin (thyroxine-binding prealbumin, TBPA) and albumin (ALB). Approximately 68% of the hormones are bound to the TBG, while 18% are bound to the TBPA and 14% bound to ALB. The amount of free or unbound hormones present is only approximately 0.03% for $T_4$ and 0.3% for $T_3$. The bound hormones are not biologically available to produce their effects. Therefore, the free hormones, although present in relatively small concentrations, are responsible for the profound biological impact of the thyroid hormones. In addition, the amount of $T_3$ and $T_4$ produced and secreted by the thyroid gland is regulated to maintain a relatively constant free hormone concentration in the plasma.

Thyrometabolic status, i.e. production of thyroid hormones and their inter-relationship and effect on the human body was originally measured by a determination of an individual's Basal Metabolic Rate (BMR). This test required meticulous and careful preparation and performance of the test frequently resulted in non-specific results.

Due to the problems inherent in measurement and interpretation of BMR, a search for laboratory alternatives was sought. As a result, evaluation and characterization of thyroid function in recent years has become the subject of elegant laboratory procedures which measure and estimate by calculation various clinically important concentrations and capacities of $T_3$, $T_4$ and the thyroxine binding proteins.

An initial laboratory test which found wide acceptance involved measurement of the total protein bound iodine (PBI) in a plasma sample. The test is based on the iodine-catalyzed reaction between ceric ions and arsenious acid. Since the majority of $T_3$ and $T_4$ in the total plasma is bound to protein, this test was considered a basic measurement of total hormonal content in a sample. Although the measurement of PBI was found clinically useful, problems were experienced due to false elevated readings resulting from iodine containing drugs. Further, PBI results did not reveal the concentration of the biologically active and important free thyroxine.

More specific tests were then developed which measured the total $T_4/T_3$ present without interference from inorganic iodine. Although $T_3$ is known to be more potent than $T_4$, $T_3$ is present in relatively small amounts (i.e., $T_4$ concentrations are typically 30-50 times $T_3$ concentrations) and, therefore, the majority of these tests are viewed as a determination of total $T_4$ with $T_3$ taking a secondary role because of its low concentration.

The methods for determining total $T_4$ include the well known serum Butanol-Extractable Iodide (BEI) technique, various ion exchange column procedures, radioimmunoassay techniques and competitive binding techniques, such as the well known Murphy-Pattee determination of total $T_4$ (Murphy, B. E. P., and Pattee, C. J.: Determination of thyroxine utilizing the property of protein-binding. J.Clin. Endocrin., 24:187, 1964).

All of the above methods are suitable for determining the total $T_4$ concentration in plasma or serum; however, none of these tests provide any information on the concentration of free $T_4$ ($FT_4$), the binding capacities and affinities of TBG, TBPA or ALB. This information, especially $FT_4$ concentration and TBG binding capacity, has been found to be significant information necessary to correctly evaluate and characterize thyroid function.

Tests have been proposed and are being presently utilized to determine $FT_4$ concentrations in plasma. The tests can be broken into two groups: those directly measuring $FT_4$ and those measuring $FT_4$ indirectly. The direct $FT_4$ measurement processes include an equilibrium dialysis method which is difficult to perform because the radioactive $T_4$ utilized in the procedure must be ultra pure. Also, another direct measurement method has been developed based on kinetic principles involving timed incubation periods and binding rates of radioactive labeled $T_4$. This method is not entirely suitable, since equilibrium conditions are not established and false readings may be introduced due to variations in measured time periods and possible reaction rate variances (Kaptein, E. M., McIntyre, S. S., et al., Free Thyroxine Estimates in Nonthyroidal Illness Comparison of Eight Methods, JCEM 52:1073 1981).

Techniques for the indirect measurement of $T_4$ include a test known as the Resin $T_3$ Uptake Test ($RT_3U$). This test measures the unsaturated sites on TBG and by calculation indirectly estimates TBG concentration. In addition, a Free $T_4$ Index may be generated from an interpretation of total $T_4$ concentration and the test results. This index may correlate with actual $FT_4$ in some cases, but many times is not a true reflection of actual $FT_4$.

As previously mentioned, competive binding techniques are known for the determination of total $T_4$ concentration. In addition, competitive binding techniques are also known for use in determining $FT_4$. For example, a method developed by Irvine involving competitive binding of $T_4$ between a partition material, such as Sephadex, and the Thyroxine Binding Proteins has been disclosed for determining $FT_4$ concentration (Irvine, C. H. G.: Measurement of free thyroxine in human serum by a Sephadex binding method. J. Clin Endocinol Metab 38:655-662, 1974).

The Irvine method is based upon and uses the ability of Sephadex to bind $T_4$ in specific amounts related to the concentration of $FT_4$ present in the serum. The method involves mixing known amounts of Sephadex, plasma or serum, physiological buffer and radioactive Thyroxine ($125_{I-T4}$) at 37 degrees C. in a test tube for 10 minutes. The Sephadex is then allowed to settle out providing an aqueous phase or supernatant and a solids phase. The solids phase includes not only the Sephadex, but also a portion of the aqueous phase absorbed, occluded, adsorbed or otherwise contained therein. The volume of aqueous phase retained in the Sephadex is known as the Inclusion Volume (I) with the supernatant volume being known as the Exclusion Volume (E). The initial Total Volume (V) of the plasma, buffer and $125_{I-T4}$ is equal to I+E.

In accordance with the Irvine method, it was found that the unbound or free $125_{I-T4}$ in the supernatant was a constant fraction of the $125_{I-T4}$ bound to the Sephadex. This fraction is believed to depend on the low affinity, but high capacity of Sephadex for $T_4$ and is unaffected by the amount of $T_4$ or protein in the sample. This partitioning ability of Sephadex is expressed as a partition coefficient ($\alpha$). Since the total amount of $125_{I-T4}$ in the system is known, measurement of radioactivity in the supernatant or aqueous phase results in a determination of the amount of $125_{I-T4}$ in the solid phase. Calculation of Free or unbound $125_{I-T4}$ can then be determined using the partition coefficient ($\alpha$). The ratio of bound to free $125_{I-T4}$ can also be determined.

As is well known, $125_{I-T4}$ distributes in a system at equlibrium in the same proportions as the $T_4$ naturally present in the plasma to provide in effect a mirror of various bound and unbound $T_4$ levels. Accordingly, a determination of naturally existing free or bound $125_{I-T4}$ concentrations in the plasma may be equated to naturally existing free or bound $T_4$ concentrations.

Although the Irvine method is quite useful in determining $FT_4$ concentration and the ratio of protein bound $T_4$ to $FT_4$ in plasma it does not provide information on clinically important TBG concentrations and binding capacities of the low affinity binding proteins.

A method which is based on the Irvine procedure has been developed by Sutherland et. al. for not only determining $FT_4$ concentration, but also determining the various binding affinities and capacities of the three Thyroxine Binding Proteins when the Total $T_4$ concentration of the plasma is already known (Sutherland R. L., Simpson-Morgan, M. W.: The thyroxine binding properties of serum proteins. A competitive binding technique employing Sephadex G-25. J. Endrocrinol. 65:319–332, 1975). The Sutherland method is based on the mass action equation $$\frac{\rho_B}{\rho_F} = \frac{C_1}{(k_1 + \rho_F)} + \frac{C_2}{(k_2 + \rho_F)} + \frac{C_3}{(k_3 + \rho_F)} \quad (1)$$

where $\rho_B$ is the concentration of bound thyroxine in the supernatant (E); $\rho_F$ is the concentration of free thyroxine in the supernatant (E); $C_1$, $C_2$ and $C_3$ are the binding capacities of TBG, TBPA and ALB respectively; and $K_1$, $K_2$, and $K_3$ are the binding affinities for TBG, TBPA and ALB respectively.

By using the Irvine method, the ratio $\rho_B/\rho_F$ can be determined; however, a single value of $\rho_B/\rho_F$ is not sufficient to solve equation 1 with its numerous variables and therefore a determination of clinically important TBG binding capacity along with the other factors is not possible.

In order to provide sufficient data points (i.e., values of $\rho_B/\rho_F$) to solve equation 1, Sutherland's method employs a "titration" of the supernatant with unlabled thyroxine. Initially, like Irvine, known amounts of plasma, buffer and $125_{I-T4}$ are mixed with partitioning material such as Sephadex. The radioactivity of the supernatant is then measured. Then a known amount of thyroxine is added to the supernatant to provide a new total $T_4$ concentration. The supernatant is again mixed for a sufficient time with the Sephadex to allow equilibrium distribution of the $125_{I-T4}$ to be reached. The radioactivity of the supernatant is again measured. This titration procedure is repeated numerous times until a sufficient number of values of $\rho_B/\rho_F$ at the various total $T_4$ concentrations are determined to define and fit a curve or function representing a solution to equation 1.

Utilizing the above titration technique, Sutherland established that the thyroxine affinities of TBG, TBPA and ALB are $8.2 \times 10^{-5}$ microgram/ml, $4.85 \times 10^{-3}$ microgram/ml, and 2.18 microgram/ml respectively.

The binding affinities are believed not to vary between individuals and are considered as a constant value for each thyroxine binding protein.

Although the Sutherland method has provided a relatively accurate determination of the concentrations, affinities and capacities important in evaluating thyroid function, it involves numerous additions of known amounts of $T_4$ and time consuming measurements of resulting $T_4$ (i.e. $125_{I-T4}$) equilibrium distribution. The method is therefore not well suited for application in commercial clinical setting to determine free $T_4$ or TBG binding capacity.

As is apparent, there are numerous clinical methods, tests and techniques presently available for measuring various biochemical factors to determine and evaluate thyrometabolic status. Although these tests and techniques provide useful tools in evaluating thyroid function, none of them have been found entirely adequate. There is therefore presently a need for a simple, commercially useful, accurate method for determining important thyroid function indicators, such as $FT_4$ concentrations and Thyroxine Binding Globulin binding capacity.

SUMMARY OF THE INVENTION

In accordance with the present invention, a simple, practical and accurate method for simultaneously determining $FT_4$ and TBG binding capacity is provided.

The present invention is an improvement upon the Sutherland competitive binding method. Instead of requiring numerous repetitive titrations followed by computer matching of the data points to a complicated equation, the present invention provides for the simultaneous determination of $FT_4$ and TBG binding capacity with a two data point determination only. The present invention is based upon a recognition that for plasma samples having $FT_4$ concentrations below certain levels, equation 1 may be simplified and solved by determining two data points only.

The method of the present invention may be summarized as follows:

(1) The determination of parameters necessary for calculation of final results. This portion of the method includes a determination of total $T_4$ concentration of the given plasma sample, a determination of the inclusion volume (I) for a known amount of partitioning material used in the method and a determination of the partition coefficient ($\alpha$) for the partitioning material. These three values may be determined by conventionally known techniques and do not form a part of the invention other than their values must necessarily be known to allow calculation of the final results.

(2) The second portion of the method involves adding radioactive thyroxine to a buffered sample of the plasma. The radioactivity ($R_0$) is then measured after a sufficient incubation and equilibrium period. Sephadex is then added to this labeled plasma sample and buffer with the radioactivity of the resulting supernatant being measured ($R_1$). Finally, a known amount of unlabeled thyroxine is added with the resulting radioactivity of the supernatant being measured ($R_2$). This portion of the procedure which determines the partitioning of labeled thyroxine between the Sephadex and supernatant at two different total thyroxine levels is similar to the repetitive titration process disclosed in Sutherland except that only one addition of unlabeled thyroxine ($T_4$) is necessary. The amount of unlabeled thyroxine must be limited as discussed below.

(3) In the third portion of the process, the parameters determined in steps 1 and 2, along with known values, such as the volume of the buffered plasma and tracer mixture, are utilized to calculate the ratio of bound thyroxine to free thyroxine ($\rho_B/\rho_F$) and the concentration of free thyroxine ($\rho_F$) in the supernatant at the two total $T_4$ concentrations of step 2. The two total $T_4$ concentrations being: total $T_4$ concentration prior to addition of the known amount of unlabeled $T_4$ ($\rho_{T4}$) and the concentration of total $T_4$ after the addition of the unlabeled $T_4$ ($\rho_{T4}'$). The second and third portions or steps may be viewed as a single step in which $\rho_B/\rho_F$ and $\rho_F$ are determined at two total $T_4$ concentrations. These values are given by $\rho_{B1}/\rho_{F1}$, $\rho_{B2}/\rho_{F2}$, $\rho_{F1}$ and $\rho_{F2}$ respectively.

(4) The values determined in step 3 of the method are then used in solving a modification of equation 1. In accordance with the present invention, when the concentration of free thyroxine in the supernatant sample ($\rho_{F4}$) is much less than $4.85 \times 10^{-3}$ microgram per milliliter ($k_2$), equation 1 may be rewritten as $$\rho_B/\rho_F = \frac{C_1}{k_1 + \rho_F} + G \qquad (2)$$

Equation 2 is identical to equation 1 except the last two terms of the equation have been combined into a constant G. Equation 2 is only valid in situations where $\rho_F$ is much less than $k_2$ and preferrably on the order of $10^{-5}$ micrograms per ml.

It is therefore an important aspect of the present invention that the determined values of $\rho_{F1}$ and $\rho_{F2}$ be compared to $k_2$. If the values for $\rho_{F1}$ and $\rho_{F2}$ are not much less than $k_2$, then equation 2 is not valid and the results from the method may not be accurate. $\rho_{F1}$ is always expected to be much less than $k_2$. This is a biological fact and is characteristic of expected natural $FT_4$ levels in serum samples. However, the concentration of $\rho_{F2}$ will increase depending upon the amount of unlabeled $T_4$ added to the sample. The amount of unlabeled $T_4$ added during the method should therefore be limited to quantities which will not raise $\rho_{F2}$ above levels which are much less than $k_2$. The comparison of $\rho_{F1}$ and $\rho_{F2}$ should be done prior to calculations using equation 2 to insure that the method produces accurate results.

Since the values for $\rho_B/\rho_F$ and $\rho_F$ are determined at two different total $T_4$ concentrations, Equation 1 can be solved to determine the two unknowns TBG capacity ($C_1$) and G. As will be realized, the values obtained by solving equation 2 will be for the supernatant only and these values must be corrected to reflect corresponding total plasma capacities.

As a feature of the present invention, not only are $FT_4$ concentrations and TBG binding capacities determined, but in addition, the value G is determined. The value G may be characterized as a measure of a particular sample's TBPA and ALB binding capacities weighted according to their respective affinities. The value G may, therefore, be of clinical significance in evaluating the contribution of the low affinity binding proteins to the thyrometabolic status.

As will be realized, the method of the present invention can be readily adapted to clinical settings where rapid analysis of numerous physiological samples is desirable wherein the analytical results provide accurate and useful information for evaluating thyroid function.

The above-discussed and many other features and attendant advantages of the present invention will become apparent as the invention becomes better understood by reference to the following detailed description when considered in conjunction with the accompanying drawings.

DETAILED DESCRIPTION OF THE INVENTION

The present invention is a method for simultaneously determining the concentration of free thyroxine ($FT_4$) and the binding capacity of thyroxine binding globulin (TBG capacity) in plasma or serum samples. The method is not applicable to the testing of whole blood. The red blood cells must be removed prior to testing to provide either plasma or, if desired, serum. In the following descriptions, reference will only be made to the testing of plasma; however, it is to be understood that the present method may be applied to both plasma and serum so that when the term plasma is used in the specification, it is intended to include serum derived from plasma.

The method of the present invention is a modification of the competitive binding method of Sutherland (see Background of the Invention). In its most basic form, the present invention involves the addition of a known amount of plasma having a known total thyroxine concentration into a buffer. A known amount of radioactive thyroxine ($125_I$-$T_4$) is added to the buffered plasma to provide a solution with radioactivity ($R_o$). This is followed by the addition of a partitioning material to the buffered radioactive plasma. The relative distribution or partitioning of the labeled $T_4$ between the known amount of added partitioning material and the remaining excluded volume (E) or supernatant is then determined by measuring the radioactivity ($R_1$) of the supernatant and relating it to $R_o$. Next, a known amount of unlabeled T4 is added to the partitioning material-solution mixture with the new distribution or partitioning of the known amount of labeled T4 being determined at the increased total T4 concentration by measuring the radioactivity of the resulting supernatant ($R_2$). The three values of measured radioactivity, ($R_o$, $R_1$ and $R_2$) along with other pre-determined parameters, are then utilized in a series of calculations to determine FT4 concentration and TBG binding capacity.

As an important step in the present process, the determined values of $\rho_{F1}$ and $\rho_{F2}$ must be compared to $4.85 \times 10^{-3}$ micrograms per ml to check the accuracy of the method. The values of $\rho_{F1}$ and $\rho_{F2}$ should be much less than $10^{-3}$ micrograms per ml and should be on the order of $10^{-4}$ or $10^{-5}$ micrograms per ml.

Figure 1:
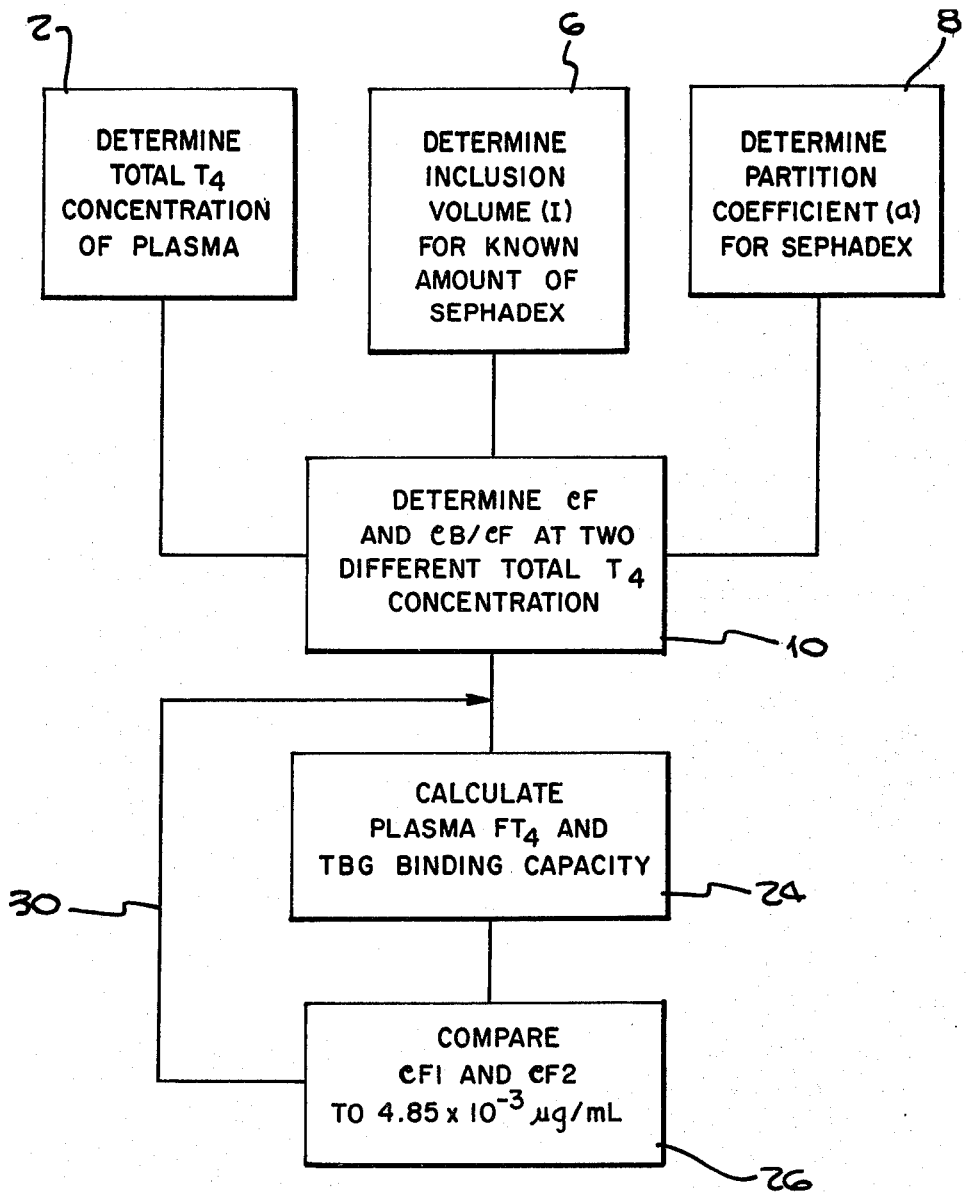
FIG. 1 is a simplified diagramatic flow representation of a method in accordance with the present invention.

Referring now to FIG. 1, a flow diagram of the present invention is shown. Basically, the method of the present invention may be conveniently separated into four basic portions or steps. The first portion represented by boxes 2, 6 and 8, relates to the conventional determination of certain parameters which are essential to allow calculation of desired results. As set forth in box 2, it is essential that the total thyroxine concentration of the plasma sample to be tested be determined. As is known, there are any number of conventional techniques for determining total T4 concentrations in plasma samples. These include radioimmunoassay techniques, serum Butanol-extractable techniques, the well known competitive binding technique of Murphy-Pattee, and various ion exchange column procedures. The particular procedure used to determine the total plasma T4 concentration is not important, so long as accurate results are provided. The determination of total T4 may be made at any time so long as the results are available when calculations in accordance with the present invention are to be made. The determination of total T4 for the plasma does not form a part of the present invention other than supplying a value which must be known in order to allow calculation of final results.

Two other values which must be determined as part of this first portion or step of the method are the inclusion volume and partition coefficient of the particular partitioning material. Many different partitioning materials are available and may be utilized in accordance with the present invention. These materials include any of the well known partitioning solids such as talc, charcoal, antibody-coated gels and the like. The preferred partitioning material is Sephadex. Methods for determining the partition coefficient and inclusion volume for Sephadex are well known. The partition coefficient ($\alpha$) is typically determined by adding a known amount of radioactive T4 to buffer without any plasma being added. The radioactivity of this labeled buffer is then measured before and after the addition of a known amount of Sephadex. The partition coefficient ($\alpha$) is then determined as is well known.

The inclusion volume (I) is equivalent to the amount of solution which is absorbed, or otherwise contained within an amount of known Sephadex when it is settled out from solution by centrifugation or otherwise. The exclusion volume (E) is equivalent to the supernatant volume which remains above the settled-out Sephadex. The exclusion volume (E) plus the inclusion volume (I) is equal to the total volume (V) of the labeled buffer and plasma solution prior to the addition of Sephadex. Methods for determining the inclusion volume (I) are well known. Typically, the inclusion volume (I) for a given amount of Sephadex is determined by the use of radioactive labeled albumin or radioactive labeled TBG.

Figure 2:
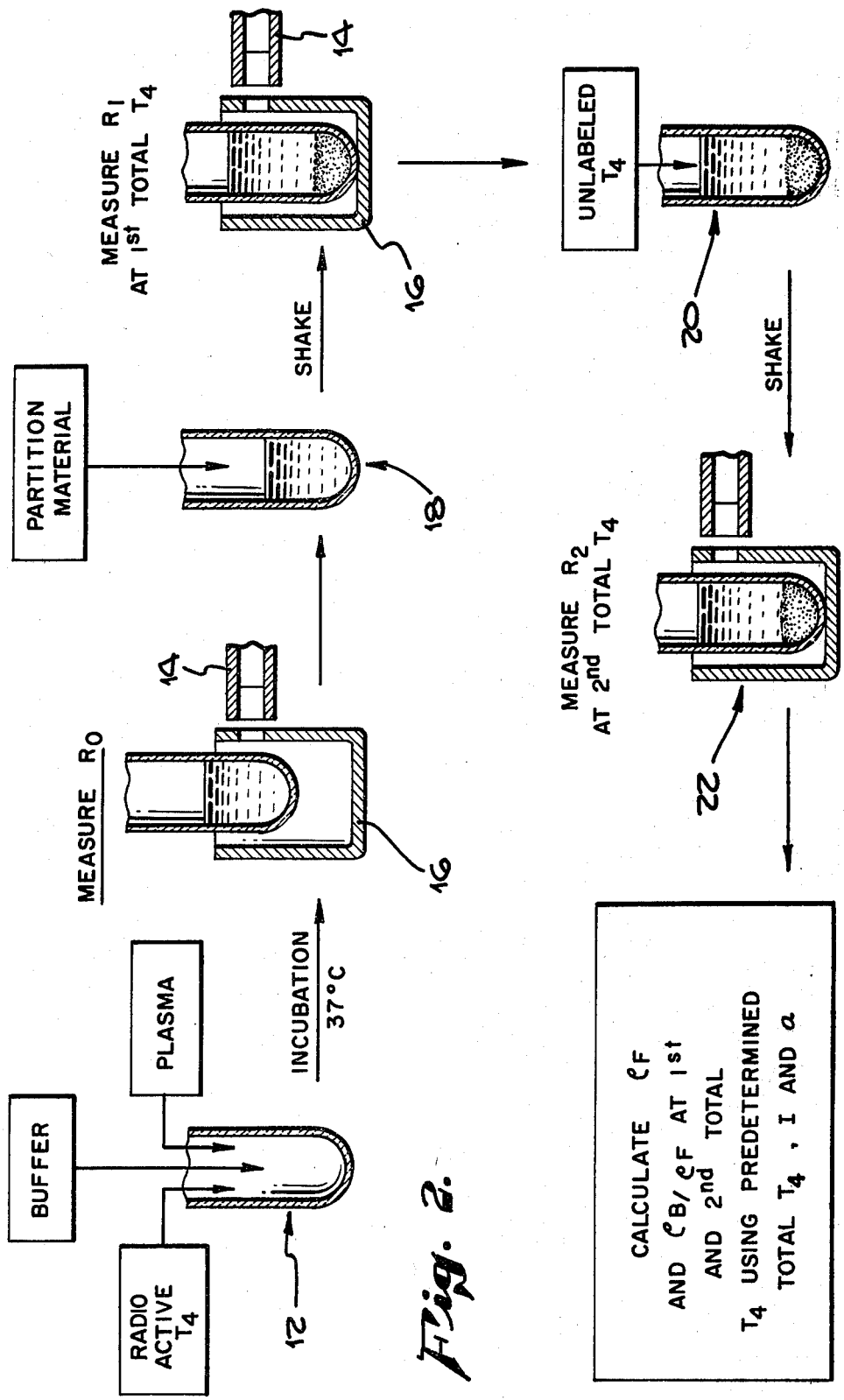
FIG. 2 is a partial diagrammatic representation of the steps in a preferred method for determining the ratio of bound thyroxine to free thyroxine and the concentration of free thyroxine in the supernatant of a Sephadex partitioned buffered sample at two different total thyroxine concentrations.

The second portion or step in accordance with the present invention is set forth in box 10. This step involves the determination of the concentration of free thyroxine in the supernatant and the ratio of bound to free thyroxine in the supernatant at the two different total T4 concentrations as discussed above. FIG. 2 is a more detailed representation of a preferred method for carrying out this second step.

As represented at 12 in FIG. 2, known amounts of a particular plasma sample to be tested, buffer and radioactive T4 are added to a test tube or other suitable container. The plasma may be any suitable plasma sample prepared by conventional blood banking separation techniques. The radioactive T4 is preferably the conventionally used iodine-125-labeled thyroxine which is commonly and conventionally used as a radioisotope tracer. The buffer may be any suitable physiologic buffer which does not change the properties of the various binding proteins and T4 when the plasma sample is diluted therein. Particularly preferred are sodium phosphate buffers at a pH of 7.4 which include around 0.1 M sodium chloride.

The labeled plasma in buffer is then incubated at a sufficient temperature and for a sufficient amount of time to allow equilibrium distribution of the radioactive T4 between the bound state and free state. As is known, labeled T4 distributes itself proportionally to the unlabeled or naturally occurring plasma T4 and therefore is a direct proportional reflection of the bound and free concentrations of T4 in the plasma sample. Typically, the incubation is carried out at a temperature of 37° C. and for a period of at least 30 minutes. Of course, the incubation temperature and time may be varied within reasonable limits so long as the properties of the various binding proteins and T4 are not affected and so long as equilibrium distribution of the radioactive T4 is achieved.

After incubation, the radioactivity of the labeled solution is measured. It should be pointed out that the activity measurements should all be made on a constant volume of supernatant as is conventional. Any conventional system may be utilized for measuring the radioactivity. For example, a suitable crystal and photomultiplier tube 14 may be utilized to measure the radioactivity present in the solution when the test tube is placed within an appropriate lead shield container 16 such that the volume of supernatant exposed in view of the crystal should be reproducibly constant. The radioactivity of the solution is given the labeled value $R_0$. Next, as shown generally at 18, a known amount of a suitable partition material is added to the solution. Many different conventional partition materials such as talc, charcoal, antibody-coated gels, and the like, may be used. The preferred partitioning material is, however, Sephadex (G-25 medium grade, untreated).

After addition of Sephadex, the mixture of Sephadex and solution is shaken at room temperature for a period of time sufficient to allow equilibrium distribution of both unlabeled and labeled T4 between the solution and Sephadex. The Sephadex is then allowed to settle to the bottom of the test tube leaving a supernatant above the solid Sephadex layer or phase.

The radioactivity of the resulting supernatant is measured and labeled $R_1$.

In the next step of the procedure, shown generally at 20, a known amount of unlabeled, non-radioactive T4 is added to the supernatant-Sephadex in the test tube. The amount of added $T_4$ must not be so great as to raise into a concentration range near $k_2$. This provides a new solution having a second known total $T_4$ concentration. The test tube is then shaken for a period of time sufficient to redistribute the labeled and unlabeled $T_4$ throughout the solid/liquid system. After equilibrium conditions have been reached (usually within 45 minutes at Room Temperature), the Sephadex is again allowed to settle out. The radioactivity of the resulting supernatant is then measured, as shown generally at 22, and given the value $R_2$.

Having determined $R_0$, $R_1$, and $R_2$, it is then possible to calculate the concentration of free $T_4$ in the supernatant and the ratio of bound $T_4$ to free $T_4$ at both total $T_4$ concentrations.

In order to carry out these calculations, the pre-determined values of total $T_4$, inclusion volume (I) and partition coefficient ($\alpha$) must be used.

The calculation of these two values at the two different total $T_4$ concentrations is as follows:

As discussed above, when a quantity of Sephadex is added to a solution containing $T_4$ and $T_4$ binding proteins, the Sephadex will absorb a volume of the buffer, the inclusion volume (I). Because of their large molecular weights, the thyroxine-binding proteins and bound $T_4$ will be concentrated in the exclusion volume (E), which is equal to the total solution volume (V) minus I (V−I). When the system is allowed to incubate until equilibrium is reached as discussed above, the $T_4$ will exist in three states, i.e., $T_4$ bound to thyroxine-binding proteins, $T_4$ bound to the Sephadex and free $T_4$ in the solution. The amount of $T_4$ in each state can be given by the concentration multiplied by the respective volume of distribution.

The above relationship of $T_4$ in the solids/liquid system may be expressed by the following equation:

$$(V-I)\rho_B + (V-I)\rho_F + \alpha\rho_F = V\rho T_4 \quad (3)$$

where $\rho_F$ = concentration of free $T_4$ in the exclusion volume; $\rho_B$ = concentration of bound $T_4$ in the exclusion volume; $\rho T_4$ = initial concentration of $T_4$ before addition of Sephadex (the product $V \times \rho T_4$ gives the total quantity of $T_4$ in the system. In equation 3, the definition of $\alpha$ is the more general definition as discussed above. It is different from the $\alpha$ as used and defined by Sutherland et al., supra.

When the Sephadex is allowed to settle, the supernatant will represent a true sample of the excluded volume (E). Measurement of the concentrations of free and bound $T_4$ in the supernatant is therefore a measure of the same concentrations in the exclusion volume (E). The concentration of $T_4$ in the supernatant, ($\rho_s$), is given by the sum of the concentrations of free and bound $T_4$ in the supernatant. The identity of the concentrations in the supernatant to those in the exclusion volume allows a relationship to be written as:

$$\rho_S = \rho_F + \rho_B \quad (4)$$

As is conventional, when a radiotracer is used to represent the stable thyroxine, $T_4$ is proportional to the count rate of the solution as measured before Sephadex is added ($R_0$), and $\rho T_4 = \epsilon R_0$; $\rho_S$ is proportional to the count rate of the supernatant after the Sephadex is added ($R_1$), and $\rho_S = \epsilon R_1$. V, I and $\alpha$ are characteristic of the system and are predetermined. Since $R_0$ and $R_1$ are measurable, equations 3 and 4 represent a solvable system of two sumultaneous equations, with two unknowns, $\rho_F$ and $\rho_B$. At the increased total $T_4$, the same two equations can be solved since $R_0$ and $R_2$ will be known at the higher $T_4$ level ($\rho T_4'$). For simplicity, however, the following discussion will relate only to $R_1$ with it being understood that the same equations also apply to a calculation of $R_2$.

Since $\alpha$, $\rho T_4$ and I are known, the free $T_4$ fraction ($\rho_F/\rho T_4$) and the bound-to-free ratio ($\rho_B/\rho_F$) can be solved in terms of $\rho_S/\rho T_4$ and therefore of $R_1$ and $R_0$ utilizing equations 3 and 4 by the following two equations.

$$\text{Free } T_4 \text{ fraction} = \frac{\rho_F}{\rho T_4} = \left[ V + \frac{\rho_S}{\rho T_4}(I - V) \right] \div \alpha \quad (5)$$

$$= \left[ V + \frac{R_1}{R_0}(I - V) \right] \div \alpha$$

$$\rho_B/\rho_F = \alpha \frac{\rho_S}{\rho T_4} \times \left[ V + \frac{\rho_S}{\rho T_4}(I - V) \right]^{-1} - 1 \quad (6)$$

$$= \alpha \frac{R_1}{R_0} \times \left[ V + \frac{R_1}{R_0}(I - V) \right]^{-1} - 1$$

These ratios are true for the radiotracer as well as the stable $T_4$. To obtain the free $T_4$ concentration one would substitute the concentration of stable $T_4$ ($\rho T_4$) into equation 5. The free $T_4$ concentration is then given by:

$$\rho_F = \rho T_4 \times \text{Free } T_4 \text{ fraction.} \quad (7)$$

An example of using the above calculations to determine $\rho_F$ and ($\rho_B/\rho_F$) at the two different total $T_4$ is as follows:

One-tenth milliliter of normal plasma ($T_4 = 7.0$ $\mu g/dl = 7$ ng/0.1 ml.$T_3U = 42\%$) and 0.1 ml of tracer I-125 $T_4$ solution were added to 14 ml of buffer in a plastic test tube. The tube was placed in a suitable apparatus and an initial count rate recorded, $R_0 = 18617$ cpm. Sephadex, 1.5 g, was added to the tube and the tube shaken gently for 45 min. The Sephadex was then allowed to settle, the tube was replaced in the counting apparatus, and the count rate from the supernatant measured, $R_1 = 20219$ cpm. The concentration of free $T_4$ and the bound to free ratio for $T_4$ in the super-natant natant was determined using equations 5, 6 and 7 by making the following substitutions:

$R_1/R_0 = 20219/18617 = 1.0861$;

$\rho T_4 = 0.007 \mu g \div 14.2$ ml $= 0.5$ ng/ml, $\alpha = 62.97$, $V = 14.2$ ml, $I = 3.403$ ml.

The result was:

$\rho_F = 0.0183$ ng/ml.

$\rho_{B1}/\rho_{F1} = 28.26$.

Unlabeled $T_4$, 73.5 ng. was then added to the tube, and again it was shaken and counted in the apparatus ($R_2=17966$ cpm). Equations 5, 6 and 7 were used again with the substitutions:

$R_2/R_0 = 17966/18617 = 0.965$, $\rho_{T4} = (0.007 + 0.0735) \div 14.2 = 5.67$ ng/ml.

The result was:

$\rho_{F2} = 0.624$ ng/ml;

$\rho_{B2}/\rho_{F2} = 15.86$.

Having determined $\rho_F$ and $\rho_B/\rho_F$ at two different total $T_4$ concentrations, the fourth step in the process may be carried out. This fourth step is represented at 24 in FIG. 1 and involves calculating the final desired values of free $T_4$ in the plasma and the TBG binding capacity. This calculation step is described as follows:

As previously discussed, the free and bound concentrations of $T_4$ are related to the capacites and affinities of the binding proteins by the equation:

$$\rho_B/\rho_F = \sum_{i=1}^{3} \frac{C_i}{k_i + \rho_F}$$

where $C_i$ and $k_i$ ($i=1,2,3$) are the capacities and affinities of TBG, TBPA, and ALB, respectively. In writing equation 1, a model in which one protein molecule has one $T_4$ binding site is assumed. Although evidence for multiple binding sites on TBPA and ALB have appeared in the literature, these apparently do not affect the calculation at physiological levels of $T_4$. Sutherland et al (supra), using a Sephadex partition method, have determined the values of the $k_i$ to be $k_i = 2 \times 10^{-5}$ microgram per/ml, $k_2 = 4.85 \times 10^{-3}$ microgram per ml, and $K_3 = 2.18$ microgram per ml. In situations where $\rho_F << k_2$, equation 7 may be simplified to:

$$\rho_B/\rho_F = \frac{C_1}{8.2 \times 10^{-5} + \rho_F} + G \quad (2)$$

where $G = C_2/k_2 + C_3/k_3$. Equation 2 can be thought of as $y = C_1 x + G$, where $y = \rho_B/\rho_F$ and $x = (8.2 \times 10^{-5} + \rho_F)^{-1}$. When x and y are known at two points, $C_1$ and G can be solved: $C_1 = y_2 - y_1/x_2 - x_1$, and $G = y_1 - C_1 x$.

The first pair of x and y is obtained by the ratio of $R_1/R_0$ and the initial quantity of $T_4$ in the plasma volume added. The second pair of x and y is obtained by the ratio of $R_2/R_0$ after a known amount (preferably about 73 ng) of $T_4$ is added to the same mixture. The amount of added $T_4$ may be increased or decreased so long as $\rho_F$ remains well below $k_2$ as previously discussed. The amount of added $T_4$ is chosen on a basis intended to provide a solution where $\rho_F$ is much less than $k_2$; however, to insure accuracy, the actual $\rho_{F2}$ must be compared to $k_2$.

The values of $C_1$ and G determined are the TBG capacities and the weighted capacities of TBPA and ALB in the exclusion volume respectively. To obtain the corresponding plasma capacities, these values must be multiplied by a dilution factor that is equal to the exclusion volume divided by the volume of plasma added to the test tube. Under physio-logical conditions, the concentration of bound $T_4$ ($BT_4$) is equal to the concentration of total $T_4$ ($T_4$) minus the concentration of free $T_4$ ($FT_4$). We can therefore write an expression relating $FT_4$ and $T_4$ in vivo:

$$\frac{T_4 - FT_4}{FT_4} = \frac{C_1}{8.2 \times 10^{-5} + FT_4} + G \quad (8)$$

Since $C_1$, G, and $T_4$ are known for the undiluted plasma, the Free $T_4$ concentration in the undiluted plasma may be determined by solving equation 8 for $FT_4$.

An example calculation is as follows:

With $\rho_F$ and $\rho_B/\rho_F$ known for two valves of total $T_4$ as calculated in the previous example calculation, $C_1$ and G in equation 2 are determined by substituting for x and y in the linear expression:

$x_1 = 10^5/(8.2 + 1.83) = 9970$, $Y_1 = 28.26$;

$x_2 = 10^5(8.2 + 62.4) = 1416$, $Y_2 = 15.86$.

$C_1$ and G were found to be $C_1 = (Y_2 - Y_1)/(x_2 - x_1) = 1.46$ ng/ml, $g = y_1 = C_1 X_1 = 13.80$.

$C_1$ is the $T_4$ binding capacity of TBG of 0.1 ml of plasma diluted to the exclusion volume ($14.2 - 3.4 = 10.8$ ml). To obtain the capacity of the undiluted plasma, we must multiply $C_1$ by the dilution factor 108, thus: TBG capacity $= 1.46$ ng/ml $\times 108 = 157$ ng/ml $= 15.76$ microgram per dl. The concentration of free $T_4$ in the undiluted plasma is obtained by making the following substitutions in equation 8: $C_1 = 157$ ng/ml, $G = 13.7 \times 108 = 1480$, Total $T_4 = 7$ ng/ml, and then solving the equation for $FT_4$: $FT_4 = 23.3$ pg/ml.

An essential step in the preferred method as shown in box 26 involves comparing the $\rho_{F1}$ and $\rho_{F2}$ to $k_2$ to insure that they are much less than this valve. This comparison is necessary to insure that the assumptions made in the calculations are correct and that the finally determined values are accurate. In the calculations example above, both $\rho_{F1}$ and $\rho_{F2}$ are much less than $K_2$(4.85 micrograms per liter) and therefore the determined value is valid. As indicated by arrow 30, this comparison step may be carried out prior to calculation of plasma $FT_4$ and TBG binding capacity. In fact, it is preferred that the comparison be made as soon as the $\rho_{F1}$ and $\rho_{F2}$ values are known. In this way, the calculation step 24 will not necessarily be carried out where the $\rho_F$ values are to high.

An Example of practice is as follows:

Plasma samples from patients in various states of thyroid function were obtained from the clinical laboratory. The following procedure was used in analyzing the various samples. Total $T_4$ was determined by conventional radioimmunoassay.

The partitioning material used as Sephadex G-25, medium grade, used untreated. Iodine-125-labeled $T_4$ was also obtained commercially. For the determination of partition coefficients ($\alpha$), it was purified by ascending paper chromatography using Whatman No. 1 paper and a solvent system of butanol: acetic acid: water (4:1:1). Otherwise it was used without purification, free iodide contamination of less that 5% being tolerated.

The method was carried out in sodium phosphate buffer (0.05M) at pH 7.4, with 0.1 M sodium chloride. The apparatus used for measuring relative activity is a modification of that of Sutherland et al (supra). Instead of a flask with a sidearm holding a constant volume for repetitive activity determination, a lead-shielded test-tube holder with an aperture for activity measurement was used. The geometry of the apparatus is such that only the same volume of supernatant can be seen by the detector. The detector, a NaI(Tl) crystal and photomultiplier tube was connected to an amplifier and a single-channel analyzer set for 35 keV, the gamma energy peak of I-125.

Twenty-milliliter plastic test tubes were filled with 14 ml of buffer, 100 microliters of plasma, and 100 microliters of a solution of buffer and I-125-labeled-$T_4$, resulting in a initial volume (before Sephadex) of V=14.2 ml. The system was allowed to incubate in a water bath at 37° C. for 1 hr, after which the tubes were placed in the measuring apparatus and the first count rate ($R_0$) measured. Sephadex (1.5 g) was then added to each tube and the tube shaken gently for 45 minutes. The Sephadex was then allowed to settle and the tubes counted again to obtain the second count rate ($R_1$). Next, a known small quantity of non-labeled $T_4$ (173.5 ng) was added to each tube and the tubes were shaken gently until a new equilibrium was reached. The tubes were counted again in the apparatus to give a third count rate ($R_2$).

The partition coefficient ($\alpha$) of Sephadex G-25 for $T_4$ was determined in parallel without any plasma added. Addition of unlabeled $T_4$ is known not to influence this coefficient. Since free iodide distributes almost equally between inclusion and exclusion volume with 9.6% bound to Sephadex, iodide contamination in the labeled $T_4$ can be routinely corrected for by subtracting $0.90 \times \%$ free iodide, from $R_0$, $R_1$ and $R_2$. Inclusion volume for 1.5 g Sephadex was determined by the use of I-131-labeled albumin as well as I-125-labeled TBG and was found to be I=3.403 ml. This value was used for all caculations. The value of $\alpha$ was determined to be 62.97 ml using I-125-$T_4$ purified by paper chromatography.

Having determined all the necessary parameters, calculation of $\rho_B/\rho_F$ and $\rho_F$ at the two total $T_4$ concentrations for each sample followed by final calculation of TBG binding capacity and $FT_4$ was carried out. The results of these tests agreed well with $FT_4$ concentrations determined by other techniques.

Figure 3:
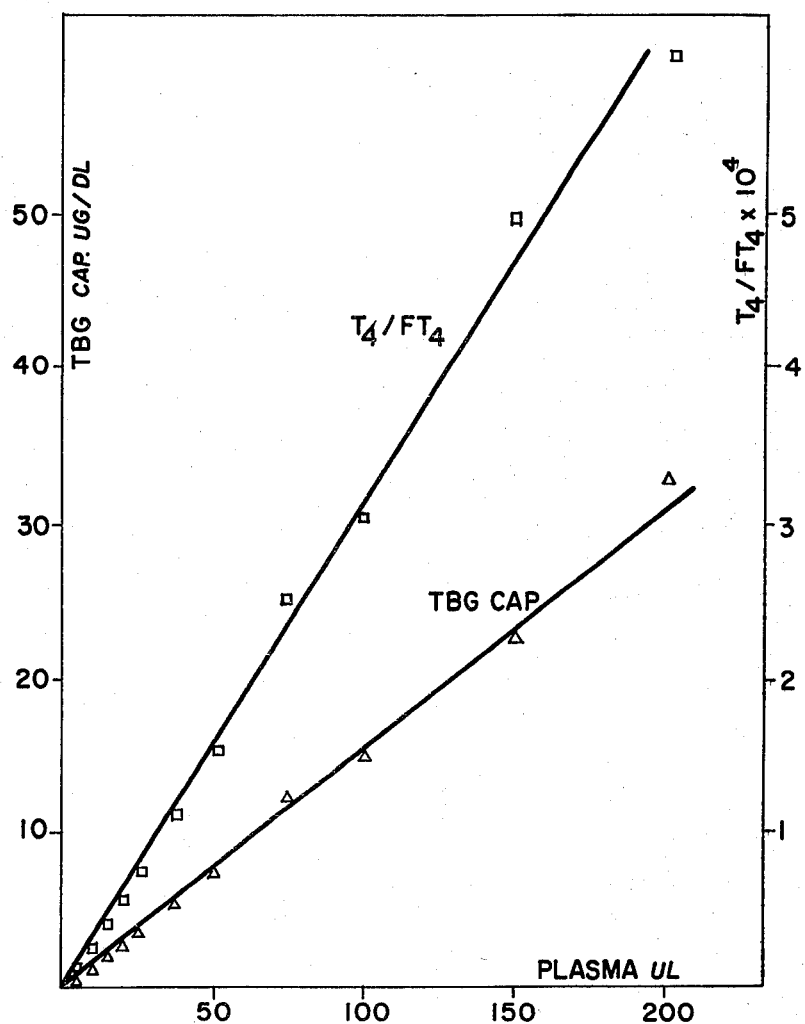
FIG. 3 is a graphic representation of exemplary experimental results.

In order to study the characteristic response to different TBG concentrations, the two-point titration method of the present invention was used to calculate $FT_4$ and TBG capacities for 11 dilutions of a normal plasma having a known total $T_4$ concentration of 7.0 microgram per deciliter. The quantities of plasma used ranged from 5 to 200 microliters per tube and the results were normalized to a standard plasma volume of 100 microliters. This represented a dilution range of from 1/20 to 2/1. The results are shown in FIG. 3. Clearly the method was found to be linear over a wide range of TBG capacities and $FT_4$ concentrations.

Having thus described exemplary embodiments of the present invention, it should be noted by those skilled in the art that the within disclosures are exemplary only and that various other alternatives, adaptations and modifications may be made within the scope of the present invention. Thus, by way of example, and not of limitation, the determinations of $R_0$, $R_1$, and $R_2$ may be carried out in parallel as opposed to a series measurement as disclosed in the preferred embodiment. For example, two identical plasma samples may be treated with buffer and radioactive $T_4$ and incubated in parallel. After a measurement of $R_0$, and addition of partition material, one sample additionally has an amount of unlabeled $T_4$ added. The two samples are shaken in parallel with the equilibrium radioactivity in the supernatant measured for each to determine the values of $R_1$ for the sample not having unlabeled $T_4$ added and $R_2$ for the sample having unlabeled $T_4$ added. Further, in measuring the radioactivity of particular supernatants, a standard portion of thesupernatant may be removed from the test tube and measured rather than reading activity in the test tube. Accordingly, the present invention is not limited to the specific embodiments as illustrated herein.

We claim:

1. A method for evaluating thyroid function from plasma having a known total thyroxine concentration, said total thyroxine concentration, including free thyroxine and bound thyroxine, said method comprising the steps of:

preparing a first solution having a known amount of radioactive thyroxine and known volumes of said plasma and a buffer, said solution having a first total thyroxine concentration ($\rho T_1$) and a first free thyroxine concentration ($\rho F_1$) where $\rho F_1$ is less than a known constant ($k_2$);

preparing a second labeled solution having a known amount of radioactive thyroxine and known volumes of said plasma and buffer, said second solution further including a known amount of added thyroxine intended to provide a secon solution having a total thyroxine concentration ($\rho T_2$) which is greater than $\rho T_1$ and a second free thyroxine concentration ($\rho F_2$) which is greater than $\rho F_1$ but less than said known constant ($k_2$);

measuring the radioactivity of said first and second solutions;

adding a known amount of partitioning material having a known partition coefficient ($\alpha$) and inclusion volume (I) to said solutions after said labeled thyroxine has reached equilibrium distribution between free and bound states;

mixing said paritioning material with said solutions for a sufficient time to allow equilibrium distribution of said labeled thyroxine between said solution and said partitioning material;

settling said partitioning material from said solutions to form first and second supernatants and first and second solids phases, said solids phases having solution equal to said inclusion volume contained therein;

measuring the radioactivity in constant fractions of said first and second supernatants; and determining the TBG binding capacity and free thyroxine concentration for said plasma from the measured radioactivity of said first and second solutions and said first and second supernatants.

2. A method according to claim 1 wherein the amounts of plasma, buffer and radioactive thyroxine in said first and second solutions are the same.

3. A method according to claim 2 wherein said second solution is prepared by adding said known amount of thyroxine to said first solution after said partitioning material has been settled from said first solution and said radioactivity of said first supernatant measured.

4. A method according to claim 1 wherein said calculation of TBG binding capacity and free thyroxine concentration includes the steps of calculating the concentration of free thyroxine ($\rho_{F1}$, $\rho_{F2}$) and the ratio of bound to free thyroxine ($\rho_{B1}/\rho_{F1}$, $\rho_{B2}/\rho_{F2}$) in said first and second supernatants respectively; and using these values to calculate the free thyroxine concentration and TBG binding capacity of said plasma.

5. A method according to claim 4 wherein calculations of $\rho_{F1}$, $\rho_{F2}$, $\rho_{B1}/\rho_{F1}$ and $\rho_{B2}/\rho_{F2}$ are provided by substituting known or determined values into the following equations $$\rho_{F1} = \rho_{T1}\left[ V_1 + \frac{R_1}{R_0}(I_1 - V_1) \right] \div \alpha$$

$$\rho_{F2} = \rho_{T2}\left[ V_2 + \frac{R_2}{R_0'}(I_2 - V_2) \right] \div \alpha$$

$$\rho_{B1}/\rho_{F1} = \alpha \frac{R_2}{R_0} \times \left[ V_1 + \frac{R_1}{R_0}(I_1 - V_1) \right]^{-1} - 1$$

$$\rho_{B2}/\rho_{F2} = \alpha \frac{R_2}{R'_0} \times \left[ V_2 + \frac{R_2}{R_0'}(I_2 - V_2) \right]^{-1} - 1$$

where $R_0$ is the activity of said first solution $R_0'$ is the activity of said second solution, $R_1$ is the activity of said first supernatant, $R_2$ is the activity of said second supernatant, said activities being measured on the same volume for each supernatant or solution and wherein $V_1$ is the volume of said first solution, $V_2$ is the volume of said second solution and $I_1$ and $I_2$ are the inclusion volumes of the partition material added to said first and second solution.

6. A method according to claim 5 wherein $V_1 = V_2$, $R_0 = R_0'$ and $I_1 = I_2$.

7. A method according to claim 5 wherein said TBG binding capacity for said plasma is determined by solving the equation $$\rho_B/\rho_F = \frac{\text{TBG Binding Capacity in Supernatant }(C_1)}{k_1 + \rho_F} + G$$

using the calculated values of $\rho_{F1}$, $\rho_{F2}$, $\rho_{B1}/\rho_{F1}$ and $\rho_{B2}/\rho_{F2}$ where $k_1$ is a known affinity constant for TBG; and multiplying the calculated value for TBG binding capacity in the supernatant by an appropriate dilution factor to obtain the TBG binding capacity for the undiluted serum.

8. A method according to claim 7 wherein calculation of said free thyroxine in said plasma is provided by substituting values of $C_1$, $G$, and total $T_4$ concentration of the plasma ($T_4$) into the following equation and solving for free thyroxine concentration ($FT_4$)

$$\frac{T_4 - FT_4}{FT_4} = \frac{C_1}{k_1 + FT_4} + G$$

9. A method for determining the binding capacity of Thyroxine Binding Globulin (TBG) and the free thyroxine concentration ($FT_4$) for a given plasma specimen where the total thyroxine concentration ($T_4$) of said plasma is known, said $T_4$ including $FT_4$ and protein bound thyroxine ($BT_4$), and said method utilizing a known amount of a partitioning material having a known Partition Coefficient ($\alpha$) and known Inclusion Volume (I), wherein the method comprises the steps of:

mixing known amounts of buffer and plasma having said known $T_4$ and radioactive thyroxine to provide a labeled sample having a known volume (V) and known total thyroxine concentration ($\rho T_4$) and free thyroxine concentration ($\rho_{F1}$);

incubating said labeled sample at a temperature and for a time sufficient to allow said radioactive thyroxine to reach equilibrium distribution in said labeled sample;

measuring the radioactivity ($R_0$) of said labeled sample;

adding said known amount of partitioning material with said known partitioning coefficient ($\alpha$) and known inclusion volume (I) to said labeled sample to form a first mixture;

aggitating said first mixture for a time sufficient to allow said radioactive thyroxine to reach equilibrium distribution between said partitioning material and said labeled sample in said first mixture;

settling out said partitioning material from said labeled sample to provide a first supernatant fraction and a solids fraction, said solids fraction including said partitioning material and said inclusion volume (I);

measuring the radioactivity ($R_1$) of said first supernatant;

adding a known amount of thyroxine to said first supernatant and solids fraction intended to form a second mixture having a second known total thyroxine concentration ($\rho T_4$) which is greater than $\rho T_4$ and a free thyroxine concentration ($\rho_{F2}$) which is greater than $\rho_{F1}$ but much less than $4 \times 10^{-3}$ microgram per ml;

aggitating said second mixture for a time sufficient to allow said radioactive thyroxine to reach equilibrium distribution between said partitioning material and said labeled sample in said second mixture;

settling out said partitioning material from said labeled sample to provide a second supernatant fraction and a solids fraction, said solids fraction including said partitioning material and said inclusion volume (I);

measuring the radioactivity ($R_2$) of said second supernatant; and determining the binding capacity of TBG and free thyroxine concentration ($FT_4$) for said plasma specimen from $R_0$ and $R_1$.

10. A method according to claim 9 wherein said partitioning material is Sephadex.

* * * * *